(12) United States Patent
Mistrello et al.

(10) Patent No.: US 10,526,365 B2
(45) Date of Patent: Jan. 7, 2020

(54) ALLERGOIDS DERIVED FROM ALLERGENES

(71) Applicant: Lofarma S.p.A., Milan (IT)

(72) Inventors: Giovanni Mistrello, Milan (IT); Daniela Roncarolo, Milan (IT); Dario Zanoni, Milan (IT); Stefania Zanotta, Milan (IT); Paolo Falagiani, Milan (IT)

(73) Assignee: LOFARMA S.P.A., Milan (IT)

( * ) Notice: Subject to any disclaimer, the term of this patent is extended or adjusted under 35 U.S.C. 154(b) by 0 days.

(21) Appl. No.: 14/691,003

(22) Filed: Apr. 20, 2015

(65) Prior Publication Data

US 2015/0259378 A1    Sep. 17, 2015

Related U.S. Application Data

(62) Division of application No. 13/059,597, filed as application No. PCT/IB2009/054325 on Oct. 2, 2009, now abandoned.

(30) Foreign Application Priority Data

Sep. 1, 2008  (IT) .............................. MI2008A1565

(51) Int. Cl.
  *C07K 17/02*    (2006.01)
  *C07K 1/107*    (2006.01)
  (Continued)

(52) U.S. Cl.
  CPC ............ *C07K 1/1077* (2013.01); *A61K 39/35* (2013.01); *A61K 39/36* (2013.01); *C07K 14/415* (2013.01);
  (Continued)

(58) Field of Classification Search
  CPC .......... A61K 2039/55566; A61K 39/35; A61K 39/36; C07K 14/415; C07K 14/435; C07K 17/02; C07K 1/1077
  See application file for complete search history.

(56) References Cited

U.S. PATENT DOCUMENTS

| 3,761,585 A | 9/1973 | Mullan et al. |
| 3,794,630 A | 2/1974 | Mullan et al. |

(Continued)

FOREIGN PATENT DOCUMENTS

| CA | 2154379 A1 | 1/1996 | |
| DE | 2039223 | 2/1971 | |
| EP | 0421949 A1 * | 4/1991 | ............. A61K 39/35 |

OTHER PUBLICATIONS

Reisner et al., Identifying Residues in Antigenic Determinants by Chemical Modification, Methods in Molecular Biology, vol. 524:103-117 (Jun. 1, 2008) with 1 page of supplemental bibliography.*

(Continued)

*Primary Examiner* — Randall L Beane
(74) *Attorney, Agent, or Firm* — Davis & Bujold PLLC; Michael J. Bujold

(57) ABSTRACT

A method of making and a modified allergen having reduced allergenicity and preserved immunogenicity compared to corresponding native allergenic material. The preserved immunogenicity is elicited by a IgG-mediated antibody response, all or part of the primary amine groups of the lysine residues of the native allergenic material are functionalized with carbamoyl or thiocarbamoyl moieties, and all or part of the primary amine groups of the arginine residues of the carbamoyl- or thiocarbamoyl functionalized allergenic material are further functionalized with dialdehyde or diketal moieties. The raw allergenic material is selected from the group consisting of DP mites extract, Der p1, ovalbumin and Lipid Transfer Protein (LTP), the average (Continued)

Assessment of the allergenic activity of Der p1 before (native) and after modification with K percentage of modified primary amine groups of the lysine ranges between 75% and 100%; and the average percentage of the substituted arginine residues ranges between 25% and 10%.

1 Claim, 12 Drawing Sheets

(51) Int. Cl.
  *A61K 39/35*  (2006.01)
  *A61K 39/36*  (2006.01)
  *C07K 14/415*  (2006.01)
  *C07K 14/435*  (2006.01)
  *A61K 39/00*  (2006.01)

(52) U.S. Cl.
  CPC ............ *C07K 14/435* (2013.01); *C07K 17/02* (2013.01); *A61K 2039/55566* (2013.01)

(56) References Cited

U.S. PATENT DOCUMENTS

| | | |
|---|---|---|
| 3,893,993 A | 7/1975 | Mullan et al. |
| 3,903,067 A | 9/1975 | Mullan et al. |
| 2007/0043512 A1 | 2/2007 | Rolph et al. |

OTHER PUBLICATIONS

Takahashi, The Reaction of Phenylglyoxal with Arginine Residues in Proteins, The Journal of Biological Chemistry, vol. 243(23):6171-6179 (1968).*

Henmar et al., Allergenicity, immunogenicity and dose-relationship of three intact allergen vaccines and four allergoid vaccines for subcutaneous vaccines grass pollen immunotherapy, Clinical & Experimental Immunology, vol. 153:316-323 (Jul. 18, 2008).*

Lund et al., "Comparison of allergenicity and immunogenicity of an intact allergen vaccine and commercially available allergoid products for birch pollen immunotherapy", Clinical and Experimental Allergy, vol. 37:564-571 (2007) Hersholm, Denmark.

Henmar et al., "Allergenicity, immunogenicity and dose-relationship of three intact allergen vaccines and four allergoid vaccines for subcutaneous grass pollen immunotherapy", Clinical and Experimental Immunology, vol. 153:316-323 (2008) Hersholm, Denmark.

Marsh et al., "Studies on 'Allergoids' Prepared from Naturally Occurring Allergens", Immunology, vol. 18:705-722 (1970) Baltimore, Maryland.

Crank et al., "Absence of seasonal variation in concentrations of the house dust mite allergen Der p1 in South Manchester homes", Thorax 47:928:931 (1982).

Lin et al., "Chemical Modification of Cationic Groups of a Novel a-Neurotoxin (Ch-4) from King Cobra . . . ", J. Biochem. 118, Feb. 27, 1995, pp. 297-301, Kaohsiung Medical College, Kaohsiung, Taiwan.

Akdis et al., "Immunological mechanisms of sublingual immunotherapy", Allergy, 2006, 61, Suppl 81, pp. 11-14, Swiss Institute of Allergy and Asthma Research, Davos, Switzerland, 2006, Blackwell Munksgaard.

Blazowski, "Anaphylactic shock because of sublingual immunotherapy overdose during third year of maintenance dose", Allergy Net, accepted for publication Sep. 5, 2007, Allergy 2008: 63: 374-381, The Authors Journal Compilation, Blackwell Munksgaard, Jaslo, Poland.

Flicker et al., "Renaissance of the Blocking Antibody concept in Type I Allergy", Int Arch Allergy Immunol 2003; 132 13-24, Vienna Austria, S. Karger AG, Basel.

Glazer, "Specific Chemical Modification of Proteins", Annu. Rev. Biochem, 1970, 39: 101-130, Los Angeles, California.

Grammer et al., "Modified forms of allergen immunotherapy", J. Allergy Clin. Immunol 76: 397-401, Aug. 1985, Chicago, Illinois.

Habeeb, "Determination of Free Amino Groups in Proteins by Trinitrobenzenesulfonic Acid", Analytical Biochemistry 14, 328-336, 1966, Buffalo, New York.

James et al., "Update on mechanisms of allergen injection immunotherapy", Jul. 8, 2008, Clinical and Experimental Allergy, 38, pp. 1074-1088, The Authors Journal Compilation, 2008 Blackwell Publishing Ltd., London, UK.

Lowry et al., "Protein Measurement with the Folin Phenol Reagent", (From the Department of Pharmacology, Washing University School of Medicine, St. Louis, Missouri), 1951, pp. 265-275.

Marsh, "Preparation and Properties of 'Allergoids' Derived from Native Pollen Allergens by Mild Formalin Treatment", Inter. Arch. Allergy 41: 199-215, 1971, Baltimore, Maryland.

Mistrello et al., "Monomeric chemically modified allergens: immunologic and physicochemical characterization", Allergy 1996: 51: 8-15, Munksgaard.

Rezvani et al., "Anaphylactic Reactions During Immunotherapy", Immunol Allergy Clin N Am 27: 295-307, 2007, Cincinnati, Ohio, Elsevier Inc.

Shah et al., "Probing structure-activity relationship in diamine oxidase-reactivies of lysine and arginine residues", International Journal of Biological Macromolecules 18, 77-81, 1996, India, Elsevier Inc.

Ventura et al., "Local and Systemic Reactions Occurring During Immunotherapy: An Epidemiological Evaluation and a Prospective Safety-Monitoring Study", Jan. 1, 2008, Immunopharmacology and Immunotoxicology, 30: pp. 153-161, Italy, Informa Heathcare USA, Inc.

Cirkovic et al., "The Influence of a residual group in low-molecular-weight allergoids of Artemisia vulgaris pollen on their allergenicity, IgE- and IgG-binding properties", Allergy 2002: 57: 1013-1020, Blackwell Munksgaars.

"Allergen Products", European Pharmacopoeia 7.0, Jan. 2010, pp. 671-672.

Grammer et al., "Polymerization and Fractionation of House Dust Mite Allergen", Allergy Proc., May-Jun. 1993, pp. 195-199, vol. 14, No. 3.

Mitra et al., "Effects of chemical reagents on the allergenicity", PubMed, Biochem Int., Feb. 1992; 26(1):25-33.

Nakada et al., "Allergenicity and immunogenicity of house-dust mite (*Dermatophagoides farinae*) antigens treated with glutaraldehyde", PubMed, Ann Allergy, May 1985; 54(5):437-41.

Salgado et al., "Characterization of Allergoids from Ovalbumin in vitro and in vivo", Immunobiol., Apr. 12, 1996, vol. 196, pp. 375-386, by Gustav Fischer Verlag.

Yamasaki et al., "Modification of Available Arginine Residues in Proteins by p-Hydroxyphenylglyoxal", Analytical Biochemistry 109, Mar. 31, 1980, pp. 32-39.

Weir M.D., Handbook of Experimental Immunology, Passive cutaneous anaphylaxis (PCA), Chapter 21.1, Second Edition, Blackwell Scientific Publications (1996).

* cited by examiner

Figure 1. Assessment of the allergenic activity of the DP extract before (native) and after modification with KCNO or KCNO/PGO

| | C50* (µl) | MOD/NAT |
|---|---|---|
| Native | 0.0012 | - |
| KCNO | 0.0223 | 18 |
| KCNO/PGO | 0.2811 | 227 |

C50: Volume of sample (microliters) that is necessary to show a 50% in

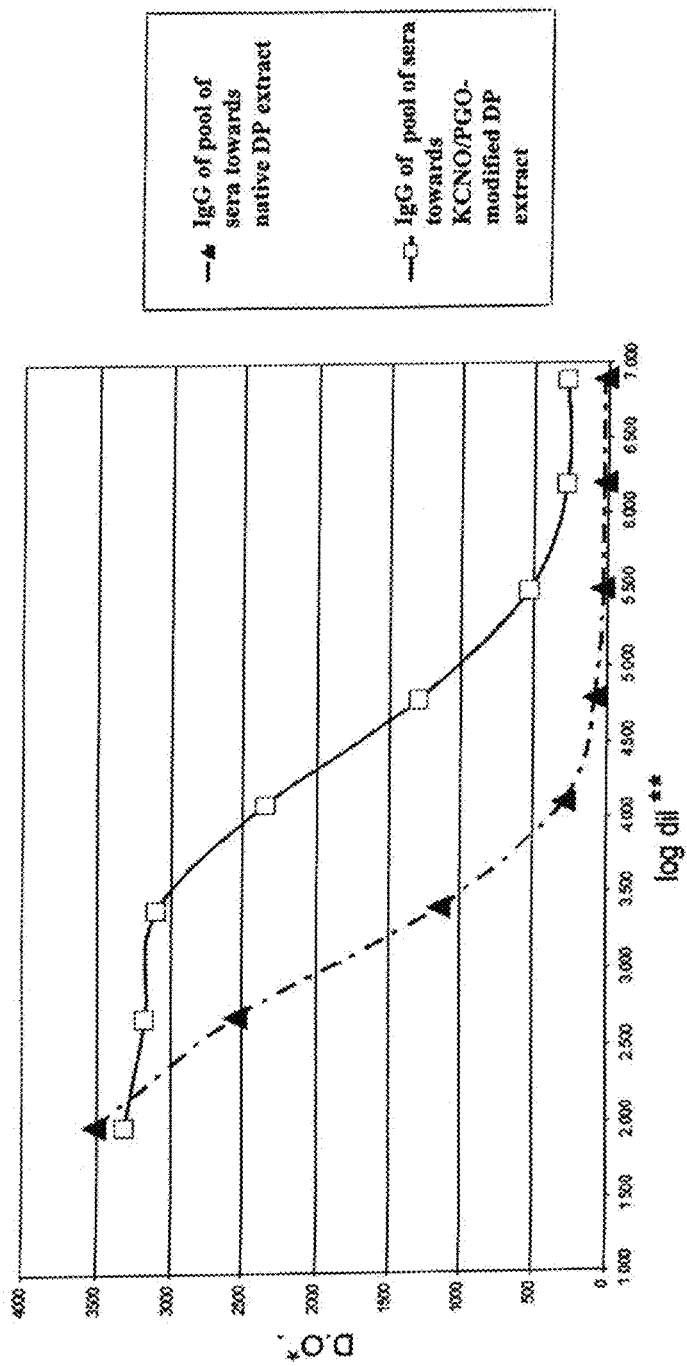
Figure 2. IgG reactivity in the serum of mice immunized with KCNO/PGO-modified DP extract

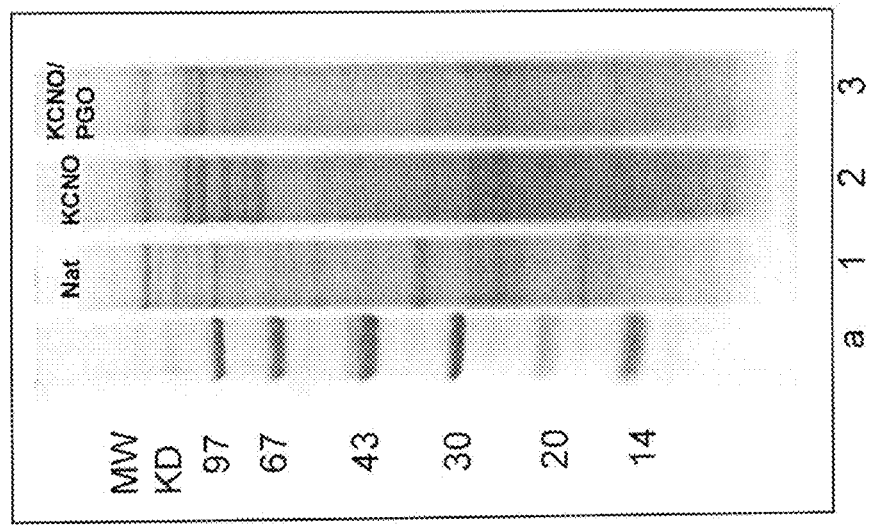
Figure 3. Protein profile of DP extract, native, KCNO-modified or KCNO-PGO modified
SDS-PAGE profile
1. native DP extract
2. KCNO-modified DP extract
3. KCNO/PGO-modified DP extract
molecular weight marker (phosphorylase B: 97KD, albumin: 67 Kd, OVA: 45 KD, carbonic anhydrase: 30 KD, trypsin inhibitor: 20 KD, alpha-lactalbumin: 14 KD)

Figure 4. Assessment of the allergenic activity of Der p1 before (native) and after modification with KCNO or KCNO/PGO

| | C50*(µl) | MOD/NAT |
|---|---|---|
| Native | 0.07 | - |
| KCNO | 1.26 | 16 |
| KCNO/PGO | 22.89 | 303 |

C50: Volume of sample (microliters) that is necessary to show a 50% inhibition of the IgE binding to the bead. Such value is inversely proportional to the allergenic activity of the sample under consideration.

The MOD/NAT column indicates by how many times the allergenic activity of the sample under consideration is reduced compared to the native counterpart.

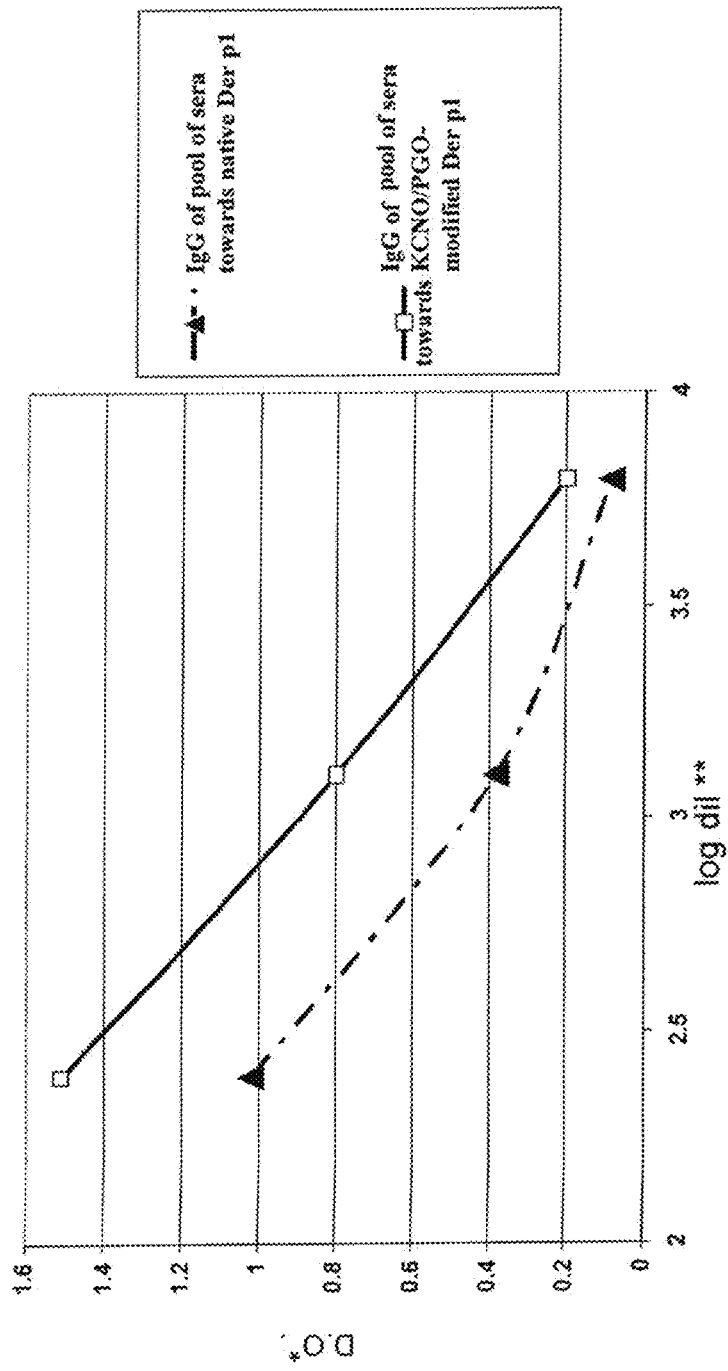

Figure 6. Profile of Der p1 allergen, native, KCNO-modified or KCNO/PGO-modified
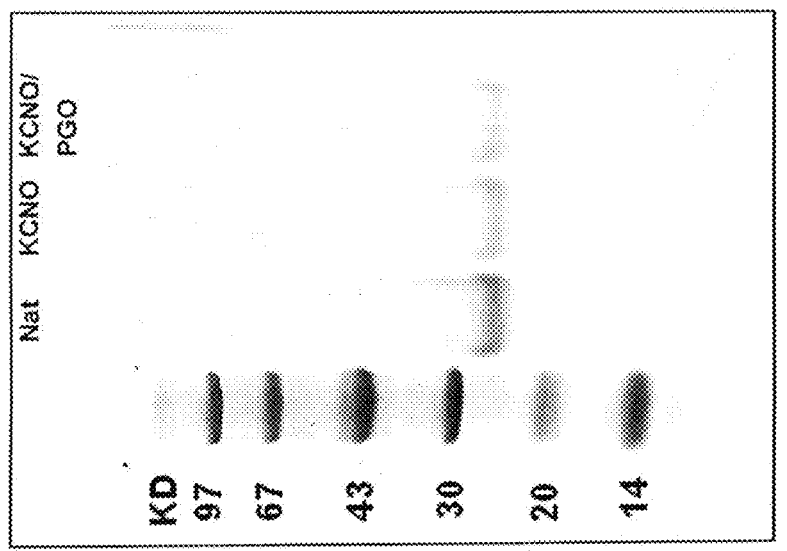

Figure 7. Assessment of the allergenic activity of Ovalbumin before (native) and after modification with KCNO or KCNO/PGO

| | C50* (µl) | MOD/NAT |
|---|---|---|
| Native | 0.016 | - |
| KCNO | 0.11 | 178 |
| KCNO/PGO | 28.09 | 1687 |

C50: Volume of sample (microliters) that is necessary to show a 50% inhibition of the IgE binding to the bead. Such value is inversely proportional to the allergenic activity of the sample under consideration.

The MOD/NAT column indicates by how many times the allergenic activity of the sample under consideration is reduced compared to the native counterpart.

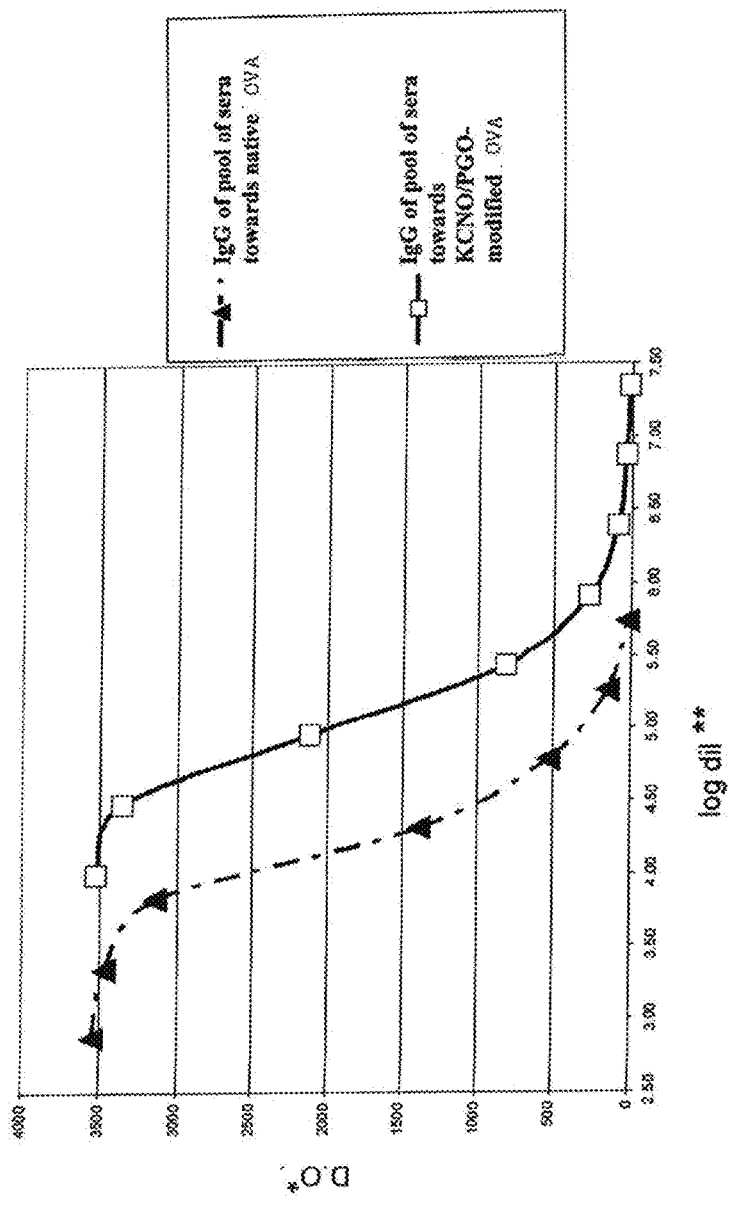
Figure 8. IgG reactivity in the serum of mice immunized with KCNO/PGO-modified Ovalbumin
Serum drawn from the immunized animals was pooled and tested in ELISA at various dilutions (from 1:1000 in base 5) against KCNO/PGO-modified OVA or against native OVA
*D.O: absorbance 450 nm
**log dil: logarithm in base 10 of the pool dilution Figure 9. Profile of Ovalbumin, native, KCNO-modified or KCNO/PGO-modified
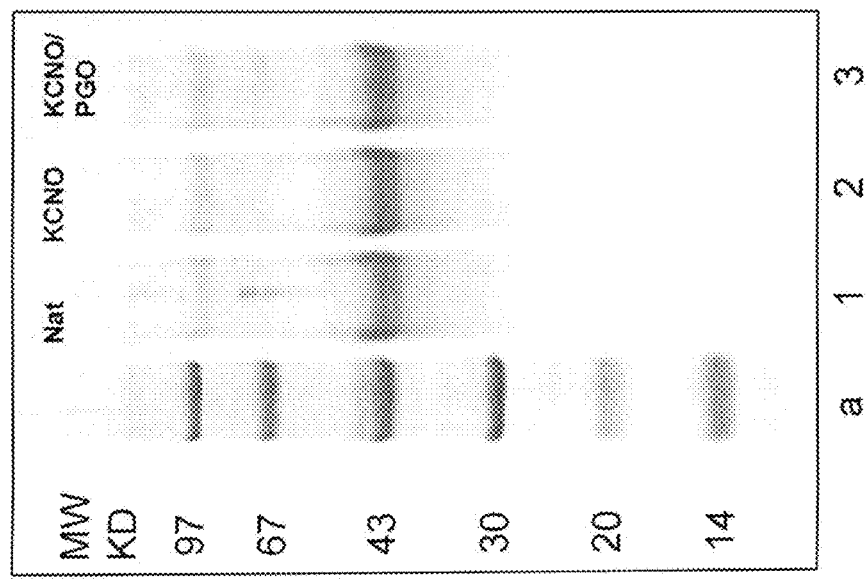
SDS-PAGE profile
1. native OVA
2. KCNO-modified OVA
3. KCNO/PGO-modified OVA
molecular weight marker (phosphorylase B: 97KD, albumin: 67 Kd, OVA: 45 KD, carbonic anhydrase: 30 KD, trypsin inhibitor: 20 KD, alpha-lactalbumin: 14 KD)

Figure 10. Assessment of the allergenic activity of recombinant Pru p3 before (native) and after modification with KCNO or KCNO/PGO

| | C50* (µl) | MOD/NAT |
|---|---|---|
| Native | 0.009 | - |
| KCNO | 0.60 | 64 |
| KCNO/PGO | 13.32 | 1422 |

C50: Volume of sample (microliters) that is necessary to show a 50% inhibition of

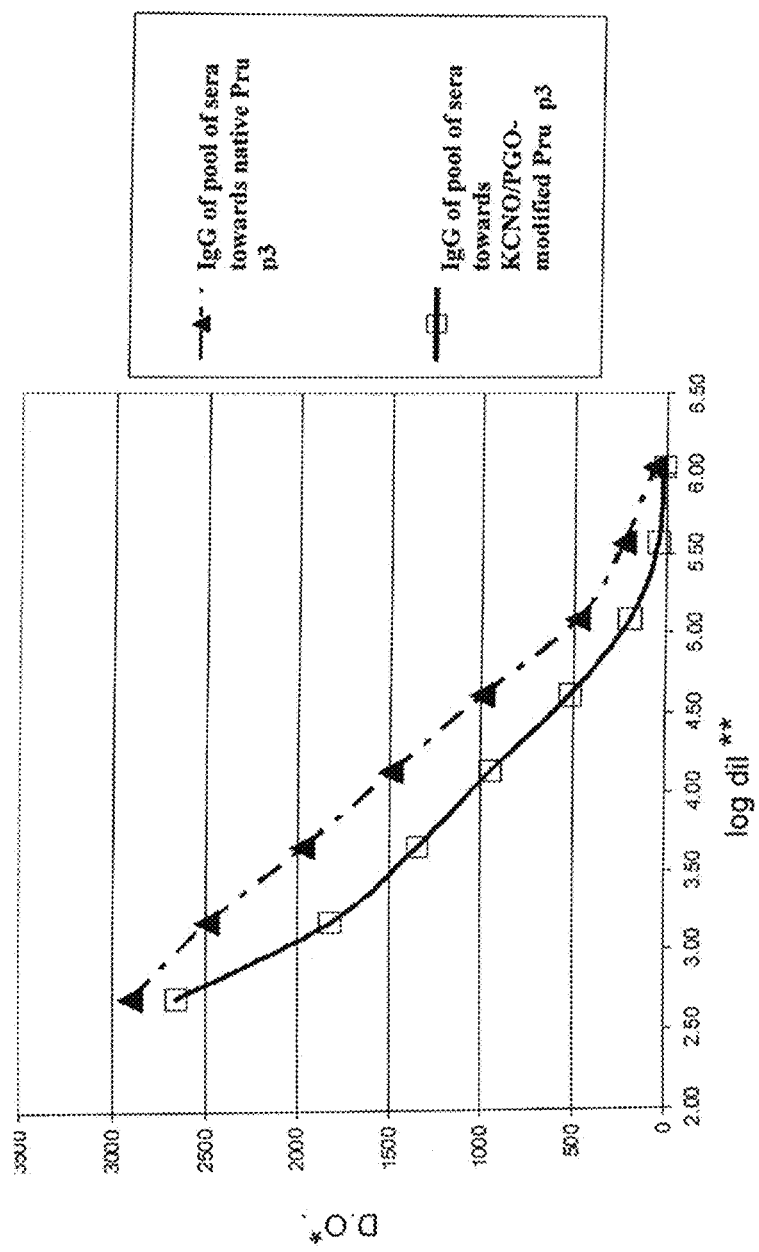
Figure 11. IgG reactivity in the serum of mice immunized with KCNO/PGO-modified recombinant Pru p3

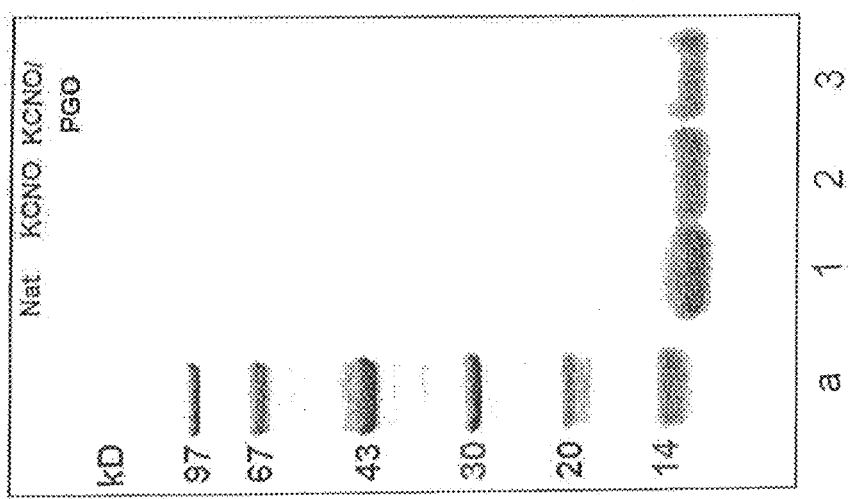
Figure 12. Profile of recombinant Pru p3 allergen before (native) or after modification with KCNO or KCNO/PGO

ALLERGOIDS DERIVED FROM ALLERGENES

FIELD OF THE INVENTION

The present invention relates to the preparation of allergoids derived from allergens by chemical functionalization, in order to reduce the risk to induce side-effects when employed as antiallergic vaccines in the immunotherapy of the allergic diseases.

BACKGROUND ART

The allergic diseases are caused by an abnormality of the immune system and are caused by the production of particular antibodies of the IgE class, specific towards ubiquitary substances (referred to by the term allergens), per se completely harmless, such as mainly pollens, mites, the epithelial derivatives, the poison of hymenoptera, fungal spores, and several foods. Such IgE antibodies are capable of linking to a specific receptor that is present on the membrane, for example, on the membrane of the mucosal mastocytes, i.e., of the basophiles, and by subsequently reacting with the allergens which they are directed to, are capable of inducing the release of mediators (among which, histamine) by the above-mentioned cells, which mediators are finally the true promoters of the allergic reaction. The allergic symptoms range from rhinitis-conjunctivitis to hives, asthma, up to anaphylactic shock, this latter being an event that can be lethal.

Recent estimates indicate that more than 20% of the population living in the industrialized countries suffers from this type of disease that, persisting in time, can determine, if it not suitably treated, a worsening of the symptoms (for example, appearance of asthma after a rhinitis) and of the sensitization that can extend to other allergens as well, which still more heavily bears on the life quality of those subjects suffering from it, and makes the identification of the more suitable therapeutic remedy to be used in the treatment of the same more complex.

The specific hyposensitization immunotherapy (ITS), unlike the pharmacological therapy, which limits itself to intervene on the symptom that then reappears in the moment when the effect of the drug ceases, is the only form of etiological treatment of the allergic diseases capable of positively bearing on the causes determining the so-called "allergic march" through the activation of some immunological mechanisms that are the basis of the clinical benefit induced by the ITS (Clin Exp Allergy. 2008; 38:1074-88. Update on mechanisms of allergen injection immunotherapy. James L K, Durham S R.; Allergy. 2006; 61 Suppl 81:11-4. Immunological mechanisms of sublingual immunotherapy. Akdis C A, Barlan I B, Bahceciler N, Akdis M.).

ITS consists in the administration in increasing doses of standardized extracts (vaccines), obtained starting from the same substance that causes the disease.

In this manner, a sort of "immunological tolerance" is progressively induced in the patient towards such substance, which is mediated by allergen-specific IgG antibodies, also termed "blocking antibodies", which, by preventing through a competition phenomenon the antibodies IgE to react with the allergen which they are directed to, inhibit the triggering of the allergic reaction and consequently inhibit the appearance of the symptoms.

The vaccines used for ITS are composed of a quite complex mixture of protein, i.e. glycoprotein, components towards which the specific IgE antibodies that an allergic subject produces are then directed.

Although the therapeutical efficacy of ITS has been shown in a number of clinical studies, it is not free from risks related to the also severe undesired reactions (Immunopharmacol Immunotoxicol. 2008; 30:153-61. Local and systemic reactions occurring during immunotherapy: an epidemiological evaluation and a prospective safety-monitoring study. Ventura M T, Giuliano G, Buquicchio R, Accettura F, Carbonara M.; Immunol Allergy Clin North Am. 2007; 27:295-307 Anaphylactic reactions during immunotherapy. Rezvani M, Bernstein D I; Allergy. 2008; 63:374. Anaphylactic shock because of sublingual immunotherapy overdose during third year of maintenance dose. Blazowski L.), which can occur following the administration of the vaccine. Such reactions may range from circumscribed local reactions (wheals, flush, itch, etc.) to systemic reactions (reaggravation of symptoms, asthma, to anaphylactic shock); although such risk has been considerably reduced by the use of slow release vaccines (delayed vaccines) or vaccines administered through alternative routes to the injective one, it anyhow limited the use of ITS in the allergic diseases therapy, currently applied on a narrow percentage compared to the entirety of the allergic patients identified following a suitable diagnostic survey.

Food allergies are also strongly increasing. Recently, unlike what has been claimed until a few years ago, whereby the only therapy against these forms of allergy appeared to be represented by the elimination of the suspected food from the diet, the idea is more and more establishing in the allergological field that the option of a specific ITS approach is suitable also for the forms of food allergy. However, it is apparent that the use of native allergens for the therapy of the food allergy forms would have the same limits (risk of undesired effects) found in the ITS of the respiratory allergy forms. In fact, such risks could even be exacerbated, since these forms of allergy often involve subjects having a few months or years of age.

In recent years, a great deal of attention has been focused on the development of vaccines that are more efficient and with a higher safety degree. Particularly, the identification of chemical modification procedures that are more or less selective, yet aimed to reduce the allergenic potential of the vaccines by preservating their immunogenic potential as much as possible, meant as the ability to induce the formation of IgG antibodies capable of recognizing, when administered to the subject, also the unmodified (native) components, which are those to which the allergic subject is exposed, and determining the development of the specific symptoms, lead to the development of the so-called allergoids (J Allergy Clin Immunol. 1985; 76:397-401. Modified forms of allergen immunotherapy. Grammer L C, Shaughnessy M A, Patterson R.; Int Arc hAllergy Appl Immunol. 1971; 41:199-215. Preparation and properties of, allergoids, derived from native pollen allergens by mild formalin treatment. Marsh D G).

The development of allergens also of food origin in the form of allergoid, and the use thereof in the immunotherapy of the specific food allergies could indeed result to be crucial in providing the allergic subject some kind of immunological tolerance, thus avoiding for the subject the occurrence of those reactions which could threaten his/her own life following the unaware ingestion of also minimal amounts of the allergen which he/she is sensitised to.

The degree of reduction of the allergenic potential of an extract induced by chemical modification can be different according to the type of reagent that is used for the modification and/or the type of extract. By using potassium cyanate as a "modifying" reagent, derivatives so-called carbamylated are obtained, which are characterized by a reduced allergenicity and a preserved immunogenicity (*Allergy*. 1996; 51:8-15. Monomeric chemically modified allergens: immunologic and physicochemical characterization. Mistrello G, Brenna O, Roncarolo D, Zanoni D, Gentili M, Falagiani P.).

However, it shall be noticed that, since the extracts subjected to chemical modification with potassium cyanate are very heterogeneous protein mixtures, the modification degree determined by the dosing of the amino groups is strictly related to the type of protein that is present, therefore the datum which is obtained expresses an average degree of modification degree. In fact, it may happen that some allergenic proteins do not significantly undergo the effect of the modification with potassium cyanate, therefore preserve much of their allergenic activity. At the level of the modified extract, the optional preservation of the allergenic activity by a component of the extract could not be shown. However, different techniques for the purification of the individual allergens have been developed for many years. Therefore, by extending the chemical modification procedure at the level of the single components, today it is possible to point out the substitution degree that can be obtained with potassium cyanate. In the case, for example, of the Der p1 allergen, one of the major allergens of the mite of the species *Dermatophagoides pteronyssinus*, which is present in the house dust, the modification degree determined by reaction with 2,4,6-trinitrobenzenesulfonic acid (TNBS) does not exceed 50%, compared to a modification degree of the extract of about 80%.

SUMMARY OF THE INVENTION

An object of the present invention is to provide a preparation for specific immunotherapy (ITS) that is provided with a higher tolerability, and particularly further minimizes the risk of possible undesired effects shown by the prior art allergoids, without thereby decreasing the desensitizing effect which is intrinsic of the conventional allergenic therapy.

Such object is achieved by means of allergoids in which the residual allergenic activity remaining after the modification with potassium cyanate or other reagent by carbamylation or thiocarbamylation reaction is further reduced thanks to a second chemical modification procedure, which provides for the use of a dialdehyde or diketone, such as phenylglyoxal or other similar reagents (glyoxal, 2,3-butanedione, 1,2-cyclohexanedione, para-hydroxyphenylglyoxal, etc.). While potassium cyanate, or other carbamylation or thiocarbamylation reagent, specifically reacts with the ε-amino groups of the lysine residues, the phenylglyoxal has as is specific target the guanidine group of the arginine residues of the proteins (Blazer A N. Specific chemical modification of proteins. Annu Rev Biochem. 1970; 39:101-30). The modification degree of the arginine residues has then been determined as described by Shah and cowork. (Shah M A, Tayyab S and Ali R. Probing Structure-activity relationship in diamine oxidase reactivities of lysine and arginine residues. Int. Journal of Biol. Macromolecules: 18; 77-81, 1996).

It has been noticed that the chemical modification of allergenic extracts or single proteins carried out by reaction with phenylglyoxal alone induces a poor reduction of the allergenic activity thereof. Similarly, the inversion of the modification sequence, phenylglyoxal and subsequently potassium cyanate, did not give encouraging results on the reduction of the allergenic potential.

DETAILED DESCRIPTION OF THE INVENTION

The specific object of the present invention is represented by modified allergens having a reduced allergenicity compared to the corresponding native allergenic material and characterized in that all or a part of the primary amine groups of the lysine and arginine residues of the allergenic molecules are functionalized as shown in the structure (I), said allergens assuming, after modification respectively with (i) carbamylation or thiocarbamylation reaction, and (ii) reaction with a dialdehyde or diketone, the following structure (I):

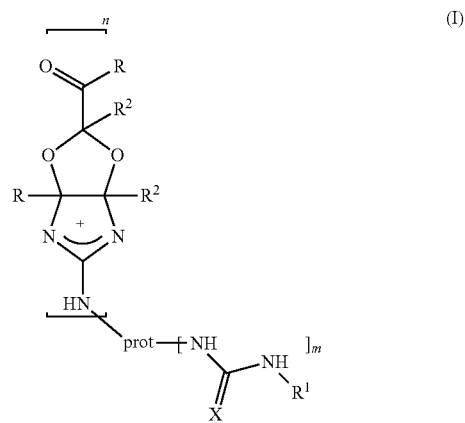

in which R and $R^2$ are independently selected from H, C1-C5 alkyl, phenyl, optionally substituted in ortho, meta, or para with a hydroxy, C1-C4 alkoxy, halogen, amino, alkylamino, dialkylamino, mercapto, C1-C4 alkylmercapto group;

X represents O, S, or NR3, where R3 is H, alkyl with 1-6 carbon atoms, phenyl, or CN;

R1 represents H, alkyl with 1-8 carbon atoms, phenyl, or arylalkyl with up to 8 carbon atoms, or alkyl containing a heterocyclic ring;

prot represents the protein residue of the allergen;

n is the number of functionalized arginine groups, and ranges between 1 and the number of arginine groups present in the allergen;

m is the number of functionalized lysine groups and ranges between 1 and the number of lysine groups present in the allergen.

Preferred modified allergens of formula (I) are those in which R is phenyl, optionally substituted in ortho, meta, or para with a hydroxy, C1-C4 alkoxy, halogen, amino, alkylamino, dialkylamino, mercapto, C1-C4 alkylmercapto group, and R2 is hydrogen.

Other preferred modified allergens are those in which X is O or S and R1 is hydrogen and, preferably, R and R2 are as defined in the previous paragraph.

Particularly preferred modified allergens are those in which R is phenyl, R1 and R2 are hydrogen, and X is O or S.

By way of example, the scheme 1 represents the reaction of lysine with potassium cyanate:

Scheme 1

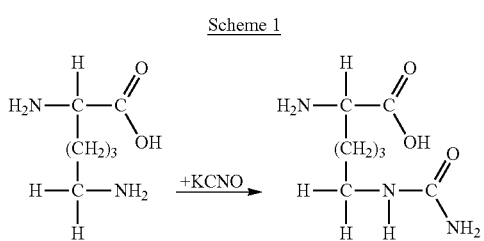

The following Scheme 2 represents an example of the functionalization reaction with phenylglyoxal of an arginine residue of the allergoid:

Scheme 2

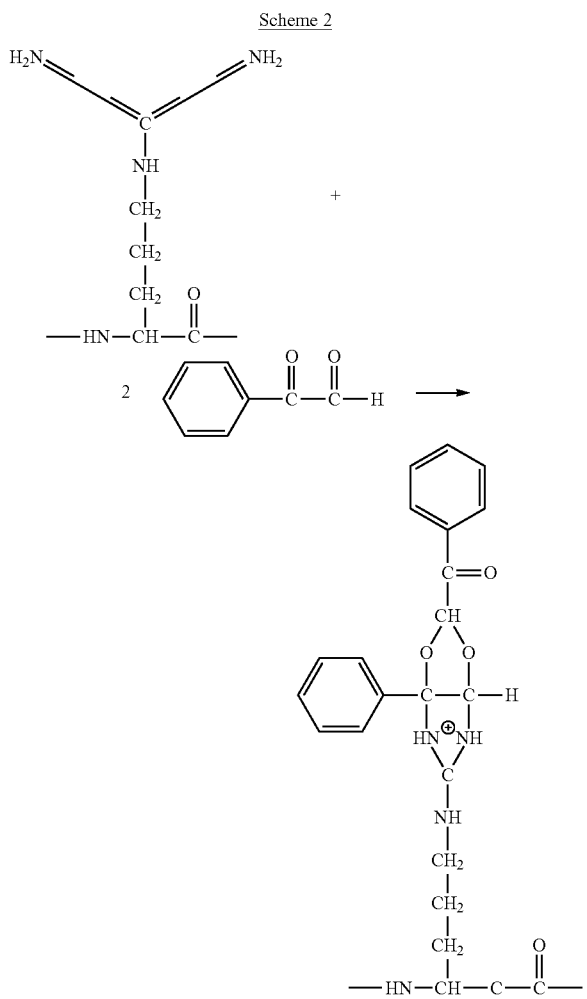

The allergenic material to be subjected to the method according to the invention can be obtained by different sources such as mites, pollens, epithelia of animals, mycophyta, proteins of food origin (milk, egg, cereals, peach, apple, etc.) by extraction of the allergenic proteins with a suitable, typically aqueous, solvent; such material can be also composed of proteins purified by the raw materials cited above, i.e., in recombinant form, produced through conventional techniques of molecular biology.

The functionalization by a carbamylation or thiocarbamylation reaction occurs by treatment with alkaline cyanate (KCNO or NaCNO), or organic isocyanates or tiocyanates.

The derivatives in which X is NR3 can be obtained starting from the compounds in which X is S by guanidylation reaction with a compound of formula R3-NH$_2$, in accordance with procedures that are conventional and known to those skilled in the art, such as, for example, the use of the Mukaijama's reagent.

For the modification of an extract with potassium cyanate (KCNO), it is suitable that the final concentration of the salt ranges between 0.1 M and 1.5 M, preferably between 0.4 M and 0.8 M, optionally keeping the pH between 7 and 11, preferably between 9 and 9.6; the temperature can range between room temperature and 50° C., preferably between 35 and 40° C., for a total reaction time between 12 and 36 hours, preferably between 16 and 24 hours. In the case of modification with organic isocyanates and isothiocyanates, which are more reactive substances, the reaction shall be performed at room temperature or below, preferably between 0° C. and 5° C., while the reaction time will be able to range between 30 minutes and 8 hours, preferably between 2 and 4 hours. Due to their poor solubility in water, the reaction will be able to be carried out in the presence of a compatible organic solvent.

At the end of the reaction, the thus-modified extract is subjected to gel-filtration to remove the excess reagent, and is equilibrated with a suitable saline solution.

The substitution degree of the —NH2 groups of the lysines that are present in the allergenic molecules composing the extract, or of the single allergic molecules purified or in a recombinant form after modification with potassium cyanate can be determined by an assay with trinitrobenzenesulfonic acid (Habeeb, Anal. Bioch. 14, 328, 1966), or by analyzing the disappearance of the lysine residues and the appearance of homocitrulline with suitable methods or instrumental analyses that are known to those skilled in the art.

For the modification with phenylglyoxal (PGO), to the samples modified with KCNO under the conditions described before, an amount of 0.1 M sodium bicarbonate is added, so as to bring the pH of the solutions to 8.0. The protein concentration of the samples ranges between 1 and 10 mg/mL (extracts), i.e., 0.1 and 2.5 mg/mL (purified proteins) as determined according to Lowry (*J. Biol. Chem*, 1970:193, 265-275. Protein measurement With Folin Phenol reagent. Lowry, Rosebrough N. J., Farr A. L., Randall R. J.). Subsequently, PGO is added to the above-mentioned solutions, so as to have a molar excess thereof ranging between 100 and 1600, preferably between 400 and 800. In order to facilitate the dissolution of the PGO, the latter has been previously dissolved in ethyl alcohol at a concentration of about 50 mg/mL. The mixture is left under mild stirring for a period of time ranging between 30 minutes and 8 hours, preferably 4 hours, at temperatures ranging between 20 and 37° C., preferably 25° C. Then, the reaction proceeds with the dialysis or the gel filtration against a suitable buffer of the thus-obtained extract. The same procedure is followed by using the other reagents modifying the arginine residues.

A similar method will be used for the functionalization with different dialdehydes or diketones.

The substitution degree of the arginine residues is assessed according to Shah. On the basis of the above-mentioned method, the substitution degree of the arginine groups is determined by considering a molar extinction coefficient of 11000 $M^{-1}cm^{-1}$, at 250 nm for the diphenyl-arginine complex, the formation of which is the consequence of the reaction with PGO.

Generally, the average percentage of modified primary amine groups shall range between 75% and 100%, typically of about 90%; while the average percentage of the substituted arginine residues shall range between 25 and 100%, typically of about 40%.

BRIEF DESCRIPTION OF THE FIGURES

FIG. 1 shows the assessment of the allergenic activity of the DP extract, native and after modification with KCNO or KCNO/phenylglyoxal;

FIG. 2 shows the IgG reactivity in the serum of mice immunized with DP extract modified with KCNO/phenylglyoxal;

FIG. 3 shows the protein profile of DP extract, native, modified with KCNO or KCNO/phenylglyoxal;

FIG. 4 shows the assessment of the allergenic activity of Der p1, native and after modification with KCNO or KCNO/phenylglyoxal;

FIG. 5 shows the IgG reactivity in the serum of mice immunized with Der p1 modified with KCNO/phenylglyoxal;

FIG. 6 shows the profile of the Der p1 allergen native, modified with KCNO or with KCNO/phenylglyoxal;

FIG. 7 shows the assessment of the allergenic activity of the Ovalbumin, native and after modification with KCNO or KCNO/phenylglyoxal;

FIG. 8 shows the IgG reactivity in the serum of mice immunized with Ovalbumin modified with KCNO/phenylglyoxal;

FIG. 9 shows the profile of Ovalbumin, native, modified with KCNO or with KCNO/phenylglyoxal;

FIG. 10 shows the assessment of the allergenic activity of recombinant Pru p3, native and after modification with KCNO or KCNO/phenylglyoxal;

FIG. 11 shows the IgG reactivity in the serum of mice immunized with recombinant Pru p3 modified with KCNO/phenylglyoxal;

FIG. 12 shows the profile of the recombinant Pru p3 allergen, native or after modification with KCNO or KCNO/phenylglyoxal.

EXPERIMENTAL SECTION

In accordance with the methods described above, allergoid samples obtained after reaction with KCNO are prepared, i.e., having the double KCNO/PGO substitution.

Subsequently, the "doubly" modified samples are compared to those modified with KCNO, i.e., native, in terms of allergenic potential by EAST-inhibition, molecular dimensions by SDS-PAGE, and immunogenic activity by ELISA.

The present invention will be now described in greater detail by way of non-limiting example, relatively to the KCNO/PGO modification procedure of some allergens both in the form of extract and single proteins purified from the extract itself, or commercial, i.e., produced in recombinant form by molecular biology techniques. As an example of allergenic extract for therapeutical use, the DP mites extract has been selected since, in virtue of their ubiquitariness, can be the cause of specific allergy all over the world. In this meaning, the DP extract can be considered representative of this class. However, the chemical modification procedure has been extended also to single purified proteins such as the allergen known as Der p1 (one of the major allergens of the DP extract obtained by a suitable purification process from the same extract), the allergenic activity of which is preserved to a large extent also after the modification with KCNO, and to purified proteins of food origin, also a cause for specific allergies that can unfortunately result lethal for the affected subject.

Therefore, two allergens of food origin have been also taken into account for our experiments: ovalbumin (OVA), a commercial protein purified from egg albumen, the latter being often the cause of a specific allergy in children; the allergen known as LTP (lipid transfer protein, Pru p3), composing the major allergen of the peach extract (but it is present in many other plant foods), and is also responsible for even severe allergic reactions. The latter allergen has been obtained in a recombinant form through the application of molecular biology techniques. Each example comes with the relative experimental tests.

Example 1

Chemical Modification Procedure of an Extract of Mites of the Genus *Dermatophagoides pteronissinus* by KCNO, i.e., a KCNO/PGO Combination in Sequence The extract of mites of the genus *Dermatophagoides pteronissinus* (Greer Labs, Lenoir, N.C., USA) has been prepared, after defatting with ethyl ether, by combining 100 mL of PBS (0.015 M phosphate buffer, 0.135 M NaCl, at pH 7.2) containing 0.05% azide (PBS-A) to 5 g of dehydrated mites bodies, and then subjecting the mixture to an ultrasonic treatment for 1 minute (Branson Ultrasonics, Sonifier 450, Darbury Conn., USA) in order to break the mites exoskeleton and to promote the extraction of the allergenic proteins contained therein. At the end, the preparation was put under stirring at 4° C. overnight. After centrifugation at 14000 rpm for 30 min and removal of the insoluble pellet, the surnatant was dialyzed against distilled $H_2O$ and freeze dried.

The freeze dried extract is then taken up in a volume of 20 mM sodium phosphate buffer, pH 6.86, so as to reach a protein concentration of 2.5 mg/mL according to Lowry. Such extract was subsequently gel-filtered on Sephadex™ G-25 (GE Healthcare Uppsala, Sweden), eluting with the same buffer and collecting the excluded peak. This operation is carried out to remove the low molecular weight compounds that could interfere in the successive chemical modification procedure. To 50 mL of such solution, 1.92 g sodium tetraborate decahydrate and 2.05 g potassium cyanate is added. The salts were brought to solution by slow stirring, and the pH was optionally adjusted to 9.3 with 1 M NaOH. The resulting solution was kept under slow stirring for 16 hours in a thermostated bath at 40° C. in a sealed flask. During the first hours, the pH was monitored and optionally adjusted by the addition of 1 M phosphoric acid. The thus-obtained preparation was gel-filtered again on G-25 column to remove the excess reagent, and sterilized on Millipore 0.22 micron membranes. A minimum part thereof was used for the successive analyses. The substitution percentage of the extract amine groups, assessed by the TNBS test, resulted to be equal to 76%. The rest of the KCNO-modified extract was subjected to a second chemical modification procedure with PGO under the experimental conditions described below.

The KCNO-modified DP extract, i.e., the DP extract before the modification at the protein concentration of 2.0 mg/mL (Lowry), is brought to pH 8 with addition of 0.1 M sodium bicarbonate. Subsequently, to the KCNO-modified sample, the PGO is added in a molar excess of 800 relative to the proteins. In order to calculate the molar excess, it being an extract and not a single protein, all the known sequences of the DP extract allergens have been unlodaded from the UniProtKB database. By considering the molecular mass of each known allergen, the number of arginine residues on the basis of the claimed aminoacid sequence and the relative amount of the various allergens on the basis of the intensity of the visible bands after SDS-PAGE of the DP extract, it has been arbitrarily established to consider for the DP extract an average molecular weight of 40 kDa and an average number of arginine residues of 15. In order to facilitate the PGO dissolution, the latter has been previously dissolved in ethyl alcohol at a 0.3 M concentration. The mixture is left under mild stirring for 4 hours at 25° C. Then, the reaction proceeds with the dialysis or the gel filtration against 20 mM PBS. The substitution degree of the arginine residues in the sample under consideration results to be equal to 37%. Subsequently, where it is possible, the KCNO/PGO-modified DP sample was compared to that modified with KCNO, i.e., native, in terms of allergenic potential by EAST-inhibition, immunogenic ability by ELISA, and molecular dimensions by SDS-PAGE.

Assessment of Allergnicity by EAST-Inhibition

To this aim, polystyrene beads, previously treated with glutaraldehyde, were activated with DP extract in the proportion of 1 µg protein per bead.

At the same time, a pool of human sera is prepared, selected from the patients who are allergic to the DP extract with clinical records of mite allergy.

To the wells of an ELISA plate, 30 µL of serial dilutions in PBS-2% BSA (diluent) of the samples under consideration (native DP extract, KCNO-modified DP extract, KCNO/PGO-modified DP extract) are added, previously brought to the same concentration, and 20 µL of the pooled sera; the mixture is left under stirring for 2 hours at room temperature. At the same time, a positive control sample is prepared, in which the inhibitor is composed of diluent. At the end of the two hours, a DP-activated bead and 50 µL PBS-2% BSA is added to each well, and the plate is kept under stirring overnight at room temperature. The beads are then washed, and 100 µL of a solution of peroxidase-conjugated anti-human IgE antibody are added to each well and incubated under stirring for 2 hours. After three washings, the development of the colorimetric reaction is obtained by adding 100 µL TMB reagent (BioFX Laboratories, Owings Mills, Md.) and by incubating for 15 minutes at 25° C. The reaction is quenched by the addition of 50 µL 1M HCl, then 100 µL of mixture from each well are transferred to a new plate, and the intensity of the developed colour is assessed by spectrophotometric reading at 450 nm.

The detected optical densities are transformed into inhibition percentages in relation to the positive control, and a graph is plotted in which the inhibition percentage is reported on the Y axis and the logarithm of the volume of sample used in the test is reported on the X axis. From the reported points, a linear regression straight line is constructed on which the IC50 value is measured, which represents the volume in microliters of sample that is necessary for a 50% inhibition of the IgE binding to the bead. Such value is inversely proportional to the allergenic potential of the sample under consideration.

The results, depicted in FIG. 1, show that the modification with KCNO reduces the allergenic activity by 18 folds, while the combined KCNO/PGO modification has a synergistic effect, reducing the allergenic activity of the DP extract by 227-folds. It is very likely that such further reduction of the allergenic activity of the DP extract after modification with KCNO/PGO may be due to the effect of the double modification on the Der p1 allergen (see Example 2).

Assessment of Immunogenicity of the KCNO/PGO-Modified DP Extract by ELISA of the Serum of Previously Immunized Mice.

a) Mice Immunization Protocol

A group of mice composed of four Balb/c strain females (Charles River) was immunized, subcutaneously, with 200 µl of an emulsion composed of 100 µL Freund complete adjuvant and 20 µg KCNO/PGO-modified DP extract in 100 µl of physiological solution. Other three boosters were performed at two-week intervals by substituting the complete adjuvant with the incomplete one. Seven days after the last immunization, a blood drawing from the mice tail is performed, and the sample is checked by ELISA as regards the anticorpal response towards the immunogen as well as the ability to recognize the native protein.

b) Test Procedure

The test is performed to verify if the KCNO/PGO-modified DP extract maintains an immunogenic potential, meant as the ability to induce in the mouse, when administered according to the protocol indicated below, an IgG response directed also towards the native, unmodified, DP extract. To this aim, equal amounts (0.25 µg) of DP extract, native or modified with KCNO/PGO, in 50 mM carbonate/bicarbonate buffer pH 9.6, are adsorbed on the wells of polystyrene plates for ELISA assays by incubation at 4° C. for 16 hours. The wells are then washed with washing solution (60 mM phosphate buffer pH 6.5 containing 0.05% Tween-20) and the free sites are saturated with diluent solution (25% horse serum, 1 mM EDTA, 0.05% Tween 20, 0.01% thiomersal in 150 mM phosphate buffer, pH 7.4). Equal aliquots (100 µL) of 10-fold serial dilutions of the mouse sera pool in diluent buffer are added to each well and incubated at 25° C. for 2 hours. After three washings, the rabbit peroxidase-conjugated anti-mouse IgG serum is added at a 1:2000 dilution in diluent buffer, the mixture is incubated at 25° C. for 1.5 hours. After three washings, the development of the colorimetric reaction is obtained by adding 100 µL TMB reagent (BioFX Laboratories, Owings Mills, Md.) and by incubating for 15 minutes at 25° C. The reaction is quenched by the addition of 100 µL of 1 N HCl and assessed by spectrophotometric reading at 450 nm. The results on the specific IgG reactivity of the pooled sera of the mice immunized with the KCNO/PGO-modified DP extract towards the proteins both of the extract used to immunize and of the unmodified (native) counterpart are shown in FIG. 2. As it can be observed, the IgG antibodies induced by the treatment with KCNO/PGO-modified DP extract are capable of recognizing also the native DP proteins (although at a lower level than that towards the modified proteins), which shows that epitopes T analogous to those present in the native DP extract are preserved in the KCNO/PGO-modified DP extract. Therefore, the KCNO/PGO-modified extract maintains the ability of suitably stimulating the immune system so as to produce specific IgG antibodies directed also towards the proteins of the native DP extract.

This observation, if related to humans, is important, since it means that the KCNO/PGO-modified DP extract, in view of a further reduction of the allergenic activity, remains potentially capable of inducing an IgG response also towards the native DP proteins, and is therefore potentially capable of inducing a clinical benefit, since the production of specific IgG antibodies is an important element in the expression of the therapeutical efficacy of ITS (*Int Arch Allergy Immunol.* 2003; 132:13-24. Renaissance of the blocking antibody concept in type I allergy., Flicker S, Valenta R).

Polyacrylamide Gel Electrophoresis (SDS-PAGE)

The electrophoresis was performed by using 4-12% gradient acrylamide gels, prepackaged and used according to the manufacturer's indications (NuPAGE® Novex® mini gels, Invitrogen, Milan). This neutral pH batch electrophoresis system allows a better resolution of the bands in the molecular weights range of our interest.

The samples of DP extract, native or modified with KCNO or KCNO/PGO, were assessed by the above-mentioned technique, under reducing conditions (presence of 5% 2-mercaptoethanol) by loading in the gel the same amount of sample (20 μg). The separation is performed by connecting the apparatus to the Microcomputer Electrophoresis Power Supply 400/1000 and applying a constant 180 mA current for about one hour. At the end, the gel is dyed with colloidal Coomassie (Colloidal Blue staining kit, Novex®, Invitrogen). The results that can be observed in FIG. 3 point out the presence of multiple bands, both in the native DP sample and in that modified with KCNO or KCNO/PGO. The SDS-PAGE profiles seem substantially similar, even if, in effect, it is difficult to assess, in a so complex sample, a possible increase of the molecular dimensions induced by the reaction with KCNO/PGO. However, in the successive examples, performed on single proteins, it is apparent that the modification with KCNO/PGO does not involve significant increases of the molecular dimensions of the proteins under investigation.

Example 2

Chemical Modification Procedure of the Major Allergen Der p1 Purified with KCNO, i.e., by a KCNO/PGO Combination a) Purification Step of the Der p1 Allergen from the DP Extract The Der p1 allergen was purified from the DP extract by affinity chromatography, using a specific monoclonal antibody (isotype IgG1, produced at the Lofarma laboratories) covalently linked to a suitable matrix, such as CNBr-Sepharose (GE Helthcare, Milan), according to the procedure suggested by the manufacturer. The Der p1 allergen, hold in a column, is eluted therefrom by using a buffer of 5 mM glycine, 50% ethylene glycol, pH 10.0. The purified allergen was quantified by spectrophotometric reading at 280 nm, by considering the molar extinction coefficient thereof ($E_{280}$) as equal to 47330, hence an absorbance value, at a concentration of 1 mg/mL, equal to 1.89. Finally, the Der p1 was freeze dried in the presence of 1% saccharose.

The freeze dried Der p1 sample is then taken up in a volume of 20 mM sodium phosphate buffer, pH 6.86, so as to reach a protein concentration of 0.2 mg/mL. For the modification with KCNO, 50.25 mg anhydrous sodium tetraborate and 101.4 mg potassium cyanate are added to 2.5 mL of Der p1 solution. The salts were brought to solution by slow stirring and the pH optionally adjusted to 9.3 with 1 M NaOH. The resulting solution was kept under slow stirring for 16 hours in a bath thermostated at 40° C. in a sealed flask. During the first hours, the pH was monitored and optionally adjusted by the addition of 1 M phosphoric acid. The thus-obtained preparation was gel-filtered again on G-25 column to remove the excess reagent, and sterilized on Millipore 0.22 micron membranes. A minimal part thereof was used for the successive analyses. The substitution percentage of the amine groups of the extract, assessed by the TNBS test, resulted to be of 50%. The rest of the KCNO-modified sample was subjected to a second chemical modification procedure with phenylglyoxal under the experimental conditions described below.

The KCNO-modified Der p1 sample at a protein concentration of 0.14 mg/mL (Abs 280 nm) is brought to pH 8 by the addition of 0.1 M sodium bicarbonate. Subsequently, PGO is added thereto in a molar excess of 800 relative to the protein. In order to calculate the molar excess, we considered for the Der p1 allergen a molecular size of 25 KD according to the UniProtKB database, from which 15 arginine residues result. In order to facilitate the PGO dissolution, the latter has been previously dissolved in ethyl alcohol at a 0.15 M concentration. The mixture is left under slight stirring for 4 hours at 25° C. Then, the reaction proceeds with the dialysis or gel filtration against 20 mM PBS. The substitution degree of the arginine residues results to be equal to 41%. Subsequently, where it is possible, the KCNO/PGO-modified Der p1 sample was compared to that modified with KCNO or with PGO or native, in terms of allergenic potential by EAST-inhibition, immunogenic ability by ELISA, and molecular dimensions by SDS-PAGE.

Assessment of Allergenicity by EAST-Inhibition

To this aim, polystyrene beads, previously treated with glutaraldehyde, were activated with Der p1 in the proportion of 1 μg protein per bead.

At the same time, a pool of human sera is prepared, selected from the patients who are allergic to the DP extract with clinical records of mite allergy.

To the wells of an ELISA plate, 30 μL of serial dilutions in PBS-2% BSA (diluent) of the samples under consideration (native Der p1, KCNO-modified Der P1, KCNO/PGO-modified Der P1), previously brought to the same concentration, and 20 μL of the pooled sera are added; the mixture is left under stirring for 2 hours at room temperature. At the same time, a positive control sample is prepared, in which the inhibitor is composed of diluent. At the end of the two hours, a bead activated with Der p1 and 50 μL PBS-2% BSA is added to each well, and the plate is kept under stirring overnight at room temperature. The beads are then washed, and 100 μL of a solution of peroxidase-conjugated anti-human IgE antibody are added to each well and incubated under stirring for 2 hours. After three washings, the development of the colorimetric reaction is obtained by adding 100 μL TMB reagent (BioFX Laboratories, Owings Mills, Md.) and by incubating for 15 minutes at 25° C. The reaction is quenched by the addition of 50 μL 1 N HCl, then 100 μL of mixture from each well are transferred to a new plate, and the intensity of the developed colour is assessed by spectrophotometric reading at 450 nm.

The detected optical densities are transformed into inhibition percentages in relation to the positive control, and a graph is plotted in which the inhibition percentage is reported on the Y axis and the logarithm of the volume of sample used in the test is reported on the X axis. From the reported points, a linear regression straight line is constructed on which the IC50 value is measured, which represents the volume in microliters of sample that is necessary for a 50% inhibition of the IgE binding to the bead. Such value is inversely proportional to the allergenic potential of the sample under consideration.

The results, depicted in FIG. 4, show that the modification with KCNO reduces the allergenic activity of the Der p1 by 16 folds, while the modification with KCNO/PGO shows a synergistic effect, reducing the allergenic activity thereof by 303 folds.

Assessment of Immunogenicity of KCNO/PGO-Modified Der P1 by ELISA of the Serum of Previously Immunized Mice a) Mice Immunization Protocol A group of mice composed of four Balb/c strain females (Charles River) are immunized, subcutaneously, with 200 μl of an emulsion composed of 100 µl Freund complete adjuvant and 20 µg KCNO/PGO-modified Der P1 in 100 µl physiological solution. Other three boosters are carried out at two-week intervals by substituting the complete adjuvant with the incomplete one. Seven days after the last immunization, a blood drawing is performed and the specific IgG anticorpal response towards the immunogen, as well as the ability to recognize the native protein, are checked by ELISA.

b) Test Procedure

The test is performed to verify if the KCNO/PGO-modified Der P1 maintains an immunogenic potential, meant as the ability to induce in the mouse, when administered according to the protocol indicated below, an IgG response directed also towards the extract of the native, unmodified Der p1. To this aim, equal amounts (0.1 µg) of Der p1, native or modified with KCNO/PGO, in 50 mM carbonate/bicarbonate buffer pH 9.6, are adsorbed on the wells of polystyrene plates for ELISA assays by incubation at 4° C. for 16 hours. The wells are then washed with washing solution (60 mM phosphate buffer pH 6.5 containing 0.05% Tween-20) and the free sites are saturated with diluent solution (25% horse serum, 1 mM EDTA, 0.05% Tween 20, 0.01% thiomersal in 150 mM phosphate buffer, pH 7.4). Equal aliquots (100 µL) of 10-fold serial dilutions of the mouse sera pool in diluent buffer are added to each well and incubated at 25° C. for 2 hours. After three washings, the rabbit peroxidase-conjugated anti-mouse IgG serum is added at a 1:2000 dilution in diluent buffer, the mixture is incubated at 25° C. for 1.5 hours. After three washings, the development of the colorimetric reaction is obtained by adding 100 µL TMB reagent (BioFX Laboratories, Owings Mills, Md.) and by incubating for 15 minutes at 25° C. The reaction is quenched by the addition of 100 µL 1 N HCl and assessed by spectrophotometric reading at 450 nm. In FIG. 5, the results on the specific IgG reactivity of the pooled sera of mice immunized with KCNO/PGO-modified Der P1 are shown, towards both the allergen used to immunize and the unmodified (native) counterpart. As it can be observed, the IgG antibodies induced by the treatment with KCNO/PGO-modified Der P1 are capable of recognizing also the native Der p1 proteins (although at a lower level than that towards the modified proteins), which shows that in the KCNO/PGO-modified Der P1 T-cell epitopes are conserved, which are analogous to those present in the native counterpart. Therefore, the KCNO/PGO-modified Der P1 maintains the ability to suitably stimulate the immune system so as to produce specific IgG antibodies directed also towards the native Der p1.

Polyacrylamide Gel Electrophoresis (SDS-PAGE)

The electrophoresis was performed by using 4-12% gradient acrylamide gels, prepackaged, and used according to the manufacturer's indications (NuPAGE® Novex® mini gels, Invitrogen, Milan). This neutral pH batch electrophoresis system allows a better resolution of the bands in the molecular weights range of our interest.

The samples of Der p 1 native or modified with KCNO or KCNO/PGO were assessed by the above-mentioned technique, under reducing conditions (presence of 5% 2-mercaptoethanol) by loading in the gel the same amount of sample (5 µg). The separation is performed by connecting the apparatus to the Microcomputer Electrophoresis Power Supply 400/1000 and applying a constant 180 mA current for about one hour. At the end, the gel is dyed with colloidal Coomassie (Colloidal Blue staining kit, Novex®, Invitrogen). The results depicted in FIG. 6 indicate that there is no difference in the profiles of the samples under consideration, therefore showing that the molecular size of the Der p1 allergen is not modified by the reactions with KCNO/PGO and that it maintains, also when modified, its monomeric form.

Example 3

Chemical Modification Procedure of the Major Allergen Ovalbumin (OVA) with KCNO, i.e., a KCNO/PGO Combination A suitable amount of commercial OVA allergen (Sigma Aldrich, Milan), purified from egg albumen, is weighted and dissolved in a volume of 20 mM sodium phosphate buffer, pH 6.86, so as to reach a protein concentration of 2 mg/mL according to Lowry. For the modification with KCNO, 50.25 mg sodium tetraborate decahydrate and 101 mg potassium cyanate are added to 2.5 mL of OVA solution. The salts were brought to solution by slow stirring and the pH optionally adjusted to 9.3 with 1 M NaOH. The resulting solution was kept under slow stirring for 16 hours in a bath thermostated at 40° C. in a sealed flask. During the first hours, the pH was monitored and optionally adjusted by the addition of 1 M phosphoric acid. The thus-obtained preparation was gel-filtered again on G-25 column to remove the excess reagent, and sterilized on Millipore 0.22 micron membranes. A minimal part thereof was used for the successive analyses. The substitution percentage of the allergen amine groups, assessed by the TNBS test, resulted to be of 82%. The rest of the KCNO-modified sample was subjected to a second chemical modification procedure with phenylglyoxal under the experimental conditions described below.

The sample of KCNO-modified OVA at a protein concentration of 1.4 mg/mL (Lowry) is brought to pH 8 by the addition of 0.1 M sodium bicarbonate. Subsequently to this, the PGO is added in a molar excess of 800 relative to the protein. In order to calculate the molar excess, we considered for the OVA allergen a molecular size of 43 KD according to the UniProtKB database, from which 15 arginine residues result. In order to facilitate the PGO dissolution, the same was previously dissolved in ethyl alcohol at a 0.3 M concentration. The mixture is left under slight stirring for 4 hours at 25° C. Then, the reaction proceeds with the dialysis or gel filtration against 20 mM PBS. The substitution degree of the arginine residues of the sample results to be equal to 35%. Subsequently, the KCNO/PGO-modified OVA sample was compared, where it was possible, to that modified with KCNO or native in terms of allergenic potential by EAST-inhibition, immunogenic ability by ELISA, and molecular dimensions by SDS-PAGE.

Assessment of Allergenicity by AST-Inhibition

To this aim, polystyrene beads, previously treated with glutaraldehyde, were activated with OVA in the proportion of 1 µg protein per bead.

At the same time, a pool of human sera is prepared, selected from the patients with clinical records of egg allergy, confirmed by specific serological test.

30 µL of serial dilutions in PBS-2% BSA (diluent) of the samples under consideration (OVA native, KCNO-modified OVA, KCNO/PGO-modified OVA), previously brought to the same concentration, and 20 µL of the pooled sera are added to the wells of an ELISA plate; the mixture is left under stirring for 2 hours at room temperature. At the same time, a positive control sample is prepared, in which the inhibitor is composed of diluent. At the end of the two hours, an OVA-activated bead and 50 µL PBS-2% BSA is added to each well, and the plate is kept under stirring overnight at room temperature. The beads are then washed, and 100 µL of a solution of peroxidase-conjugated anti-human IgE antibody are added to each well and incubated under stirring for 2 hours. After three washings, the development of the colorimetric reaction is obtained by adding 100 µL TMB reagent (BioFX Laboratories, Owings Mills, Md.) and by incubating for 15 minutes at 25° C. The reaction is quenched by the addition of 50 µL 1 N HCl, then 100 µL of mixture from each well are transferred to a new plate, and the intensity of the developed colour is assessed by spectrophotometric reading at 450 nm.

The detected optical densities are transformed into inhibition percentages in relation to the positive control, and a graph is plotted in which the inhibition percentage is reported on the Y axis and the logarithm of the volume of sample used in the test is reported on the X axis. From the reported points, a linear regression straight line is constructed on which the IC50 value is measured, which represents the volume in microliters of sample that is necessary for a 50% inhibition of the IgE binding to the bead. Such value is inversely proportional to the allergenic potential of the sample under consideration.

The results, depicted in FIG. 7, show that the modification with KCNO reduces the allergenic activity of OVA by 178 folds, while the modification with KCNO/PGO induces a further reduction of the allergenic activity of OVA, more precisely by 1687 folds, showing also in this case that the sequential KCNO/PGO combination acts by a synergistic effect.

Assessment of Immunogenicity of KCNO/PGO-Modified OVA by ELISA of the Serum of Previously Immunized Mice a) Mice Immunization Protocol A group of mice composed of four Balb/c strain females (Charles River) are immunized subcutaneously with 200 µl of an emulsion composed of 100 µl Freund complete adjuvant and 20 µg KCNO/PGO-modified OVA in 100 µl physiological solution. Other three boosters are carried out at two-week intervals by substituting the complete adjuvant with the incomplete one. Seven days after the last immunization, a blood drawing from the mice tail is performed, and the anticorpal response towards the immunogen, as well as the ability to recognize the native protein, are checked by ELISA.

b) Test Procedure

The test is performed to verify if the OVA allergen modified with KCNO/PGO maintains an immunogenic potential, meant as the ability to induce in the mouse, when administered according to the protocol indicated below, an IgG response directed also towards the native, unmodified OVA. To this aim, equal amounts (0.1 µg) of OVA, native or modified with KCNO/PGO, in 50 mM carbonate/bicarbonate buffer pH 9.6 are adsorbed on the wells of polystyrene plates for ELISA assays by incubation at 4° C. for 16 hours. The wells are then washed with washing solution (60 mM phosphate buffer pH 6.5 containing 0.05% Tween-20) and the free sites are saturated with diluent solution (25% horse serum, 1 mM EDTA, 0.05% Tween 20, 0.01% thiomersal in 150 mM phosphate buffer, pH 7.4). Equal aliquots (100 µL) of 10-fold serial dilutions of the mouse sera pool in diluent buffer are added to each well and incubated at 25° C. for 2 hours. After three washings, the serum of rabbit peroxidase-conjugated anti-mouse IgG serum is added at a 1:2000 dilution in diluent buffer, the mixture is incubated at 25° C. for 1.5 hours. After three washings, the development of the colorimetric reaction is obtained by adding 100 µL TMB reagent (BioFX Laboratories, Owings Mills, Md.) and by incubating for 15 minutes at 25° C. The reaction is quenched by the addition of 100 µL of 1 N HCl and assessed by spectrophotometric reading at 450 nm. The results on the specific IgG reactivity of the pooled sera of the mice immunized with KCNO/PGO-modified OVA towards both the allergen used to immunize and the unmodified (native) counterpart are shown in FIG. 8. As it shall be noticed, the IgG antibodies induced by the treatment with KCNO/PGO-modified OVA are capable of recognizing also the native OVA proteins (although at a lower level than that towards the modified proteins), which shows that in KCNO/PGO-modified OVA T-cell epitopes are conserved, which are analogous to those present in the native counterpart. Therefore, KCNO/PGO-modified OVA maintains the ability of suitably stimulating the immune system so as to produce specific IgG antibodies directed also towards the native OVA.

Polyacrylamide Gel Electrophoresis (SDS-PAGE)

The electrophoresis was performed by using 4-12% gradient acrylamide gels, prepackaged, and used according to the manufacturer's indications (NuPAGE® Novex® mini gels, Invitrogen, Milan). This neutral pH batch electrophoresis system allows a better resolution of the bands in the molecular weights range of our interest.

The samples of native OVA or modified with KCNO or with KCNO/PGO were assessed by the above-mentioned technique, under reducing conditions (presence of 5% 2-mercaptoethanol) by loading in the gel the same amount of sample (5 Ng). The separation is performed by connecting the apparatus to the Microcomputer Electrophoresis Power Supply 400/1000 and by applying a constant 180 mA current for about one hour. At the end, the gel is dyed with colloidal Coomassie (Colloidal Blue staining kit, Novex®, Invitrogen). The results in FIG. 9 show that the reaction with KCNO/PGO does not involve significant variations of the molecular size of the OVA allergen, which maintains, also when it is modified, its monomericity.

Example 4

Chemical Modification Procedure of the Major Peach Allergen Pru p3 Obtained in Recombinant Form with KCNO or with a KCNO/PGO Combination Production Step of the rPru p r Allergen in *E. coli*

Pru p3 cDNA is obtained by amplification of the nucleotide sequence AY792996 contained in the PP LEa0029C22F clone (GenBank, Acc. No. BU047210), provided by the Genomics Institute of Clemson University (USA). The oligonucleotides used in the PCR (polymerase chain reaction) amplification reaction are Pru p 3-6H ECO (5' ccg gaa ttc cat atg cat cac cat cac cat cac ata aca tgt ggc caa gtg), and Pru p 3 Bam (5' cgc gga tcc tca ctt cac ggt ggc gc), corresponding to the 5' and 3'-terminal sequences of the transcript corresponding to the mature protein. The underscored sequences are the cleavage sites of the restriction enzymes Eco R I, Nde I, and Bam H I, necessary for the cloning in the amplification and expression vectors, the sequence codificating for six histidine residues is highlighted in italics. The obtained cDNA, after purification, was inserted in the expression vector, amplified, and sent to verify the sequence correctness by automatic sequencing (M-Medical/MWG-Biotech).

The Pru p 3 expression occurs in *Escherichia coli* BL21 Origami (DE3) cells (Stratagene), grown at 37° C. in the presence of antibiotics (100 µg/mL Amp, 15 µg/mL Kan, and 12.5 µg/mL Tet), to a density corresponding to OD600=0.6, and is induced by the addition of 1 mM IPTG to the culture medium. After growth for 16 hours at 25° C., the cells are collected by centrifugation, resuspended in 50 mM NaH2PO4, pH 8, and lysed by sonication. The soluble recombinant proteins, separated from the insoluble debris by centrifugation, are purified by affinity chromatography on NiNTA Agarose column (Qiagen, Italy), which links the histidine sequence, following the manufacturer's instructions.

The thus-purified protein, with a purity degree above 98% as shown by the SDS-PAGE profile, is quantified by spectrophotometric reading at 280 nm, by considering its molar extinction coefficient ($E_{280}$) as equal to 3480, hence the absorbance at a concentration of 1 mg/mL equal to 0.345. Finally, the Pru p3 solution is dialyzed against $H_2O$ and then freeze dried in the presence of 1% saccharose.

The freeze dried rPru p3 sample is then taken up in a volume of 20 mM sodium phosphate buffer, pH 6.86, so as to reach a protein concentration of 0.7 mg/mL. For the modification with KCNO, 50.25 mg sodium tetraborate decahydrate and 101.4 mg potassium cyanate are added to 2.5 mL of rPru p3 solution. The salts were brought to solution by slow stirring and the pH optionally adjusted to 9.3 with 1 M NaOH. The resulting solution was kept under slow stirring for 16 hours in a bath thermostated at 40° C. in a sealed flask. During the first hours, the pH was monitored and optionally adjusted by the addition of 1 M phosphoric acid. The thus-obtained preparation was gel-filtered again on G-25 column to remove the excess reagent, and sterilized on Millipore 0.22 micron membranes. A minimal part thereof was used for the successive analyses. The substitution percentage of the amine groups of Pru p3, assessed by the TNBS test, resulted to be equal to 74%. The rest of the KCNO-modified sample was subjected to a second chemical modification procedure with phenylglyoxal under the experimental conditions described below.

The KCNO-modified Pru p3 sample at a protein concentration of 0.5 mg/mL is brought to pH 8 by the addition of 0.1 M sodium bicarbonate. Subsequently to this, the PGO is added in a molar excess of 800 relative to the protein. In order to calculate the molar excess, we considered for the Pru p3 allergen a molecular size of 10 KD according to the UniProtKB database, from which 4 arginine residues result. In order to facilitate the PGO dissolution, the same was previously dissolved in ethyl alcohol at a 0.3 M concentration. The mixture is left under slight stirring for 4 hours at 25° C. Then, the reaction proceeds with the dialysis or gel filtration against 20 mM PBS. The substitution degree of the arginine residues results to be equal to 50%. Subsequently, the KCNO/PGO-modified Pru p3 sample was compared to that modified with KCNO or native in terms of allergenic potential by EAST-inhibition, immunogenic ability by ELISA, and molecular dimensions by SDS-PAGE.

Assessment of Allergenicity by EAST-Inhibition

To this aim, polystyrene beads, previously treated with glutaraldehyde, were activated with Pru p3 in the proportion of 1 µg protein per bead.

At the same time, a pool of human sera is prepared, selected from the patients with clinical records of peach allergy, confirmed by specific serological test.

To the wells of an ELISA plate, 30 µL of serial dilutions in PBS-2% BSA (diluent) of the samples under consideration (native Pru p3, KCNO-modified Pru p3, KCNO/PGO-modified Pru p3), previously brought to the same concentration, and 20 µL of the pooled sera are added; the mixture is left stirring for 2 hours at room temperature. At the same time, a positive control sample is prepared, in which the inhibitor is composed of diluent. At the end of the two hours, a bead activated with Pru p3 and 50 µL PBS-2% BSA is added to each well, and the plate is kept under stirring overnight at room temperature. The beads are then washed, and 100 µL of a solution of peroxidase-conjugated anti-human IgE antibody are added to each well and incubated under stirring for 2 hours. After three washings, the development of the colorimetric reaction is obtained by adding 100 µL TMB reagent (BioFX Laboratories, Owings Mills, Md.) and by incubating for 15 minutes at 25° C. The reaction is quenched by the addition of 50 µL 1 N HCl, then 100 µL of mixture from each well are transferred to a new plate, and the intensity of the developed colour is assessed by spectrophotometric reading at 450 nm.

The detected optical densities are transformed into inhibition percentages in relation to the positive control, and a graph is plotted in which the inhibition percentage is reported on the Y axis and the logarithm of the volume of sample used in the test is reported on the X axis. From the reported points, a linear regression straight line is constructed on which the IC50 value is measured, which represents the volume in microliters of sample that is necessary for a 50% inhibition of the IgE binding to the bead. Such value is inversely proportional to the allergenic potential of the sample under consideration.

The results, depicted in FIG. 10, show that the modification with KCNO reduces the allergenic activity of the rPru p3 allergen by 64 folds, while the modification with KCNO/PGO further reduces the above-mentioned activity, which results to be 1422 folds lower than the native counterpart.

Assessment of Immunogenicity of the KCNO/PGO-Modified Pru p3 Allergen by ELISA of the Serum of Previously Immunized Mice a) Mice Immunization Protocol A group of mice composed of four Balb/c strain females (Charles River) is immunized subcutaneously with 200 µl of an emulsion composed of 100 µl Freund complete adjuvant and 20 g KCNO/PGO-modified Pru p3 in 100 µl physiological solution. Other three boosters are carried out at two-week intervals by substituting the complete adjuvant with the incomplete one. Seven days after the last immunization, a blood drawing from the mice tail is performed, and the anticorpal response towards the immunogen, as well as the ability to recognize the native protein, is checked by ELISA.

b) Test Procedure

The test is performed to verify if the KCNO/PGO-modified Pru p3 maintains an immunogenic potential, meant as the ability to induce in the mouse, when administered according to the protocol indicated below, an IgG response directed also towards the native, unmodified Pru p3. To this aim, equal amounts (0.1 µg) of Pru p3 native or modified with KCNO/PGO, in 50 mM carbonate/bicarbonate buffer, pH 9.6, are adsorbed on the wells of polystyrene plates for ELISA assays by incubation at 4° C. for 16 hours. The wells are then washed with washing solution (60 mM phosphate buffer pH 6.5 containing 0.05% Tween-20) and the free sites are saturated with diluent solution (25% horse serum, 1 mM EDTA, 0.05% Tween 20, 0.01% thiomersal in 150 mM phosphate buffer, pH 7.4). Equal aliquots (100 µL) of 10-fold serial dilutions of the mouse sera pool in diluent buffer are added to each well and incubated at 25° C. for 2 hours. After three washings, the serum of rabbit peroxidase-conjugated anti-mouse IgG serum is added at a 1:2000 dilution in diluent buffer, the mixture is incubated at 25° C. for 1.5 hours. After three washings, the development of the colorimetric reaction is obtained by adding 100 µL TMB reagent (BioFX Laboratories, Owings Mills, Md.) and by incubating for 15 minutes at 25° C. The reaction is quenched by the addition of 100 µL 1 N HCl and assessed by spectrophotometric reading at 450 nm. The results on the specific IgG reactivity of the pooled sera of the mice immunized with KCNO/PGO-modified Pru p3 both towards the Pru p3 used to immunized and the unmodified (native) counterpart are shown in FIG. 11. As it can be observed, in FIG. 11 the IgG antibodies induced by the treatment with KCNO/PGO-modified Pru p3 are capable of recognizing also the native Pru p3 proteins, which shows that in the KCNO/PGO-modified Pru p3 T-cell epitopes are conserved, which are analogous to those present in the native counterpart. Therefore, the KCNO/PGO-modified Pru p3 maintains the ability of suitably stimulating the immune system so as to produce specific IgG antibodies directed also towards the native Pru p3.

Polyacrylamide Gel Electrophoresis (SDS-PAGE)

The electrophoresis was performed by using 4-12% gradient acrylamide gels, prepackaged and used according to the manufacturer's indications (NuPAGE® Novex® mini gels, Invitrogen, Milan). This neutral pH batch electrophoresis system allows a better resolution of the bands in the molecular weights range of our interest.

The samples of Pru p3 native or modified with KCNO or KCNO/PGO were assessed by the above-mentioned technique, under reducing conditions (presence of 5% 2-mercaptoethanol) by loading in the gel the same amount of sample (5 µg). The separation is performed by connecting the apparatus to the Microcomputer Electrophoresis Power Supply 400/1000 and applying a constant 180 mA current for about one hour. At the end, the gel is dyed with colloidal Coomassie (Colloidal Blue staining kit, Novex®, Invitrogen). The results in FIG. 12 show that the molecular size of the allergen rPru p3 does not change after the modification with KCNO/PGO, thereby maintaining its monomeric form.

The allergenic extract or the single purified proteins modified as described above can be used in the therapy of allergic patients, and administered via the parenteral route, or nasal, or sublingual or oromucosal or oral or bronchial, with a suitable device. The above-mentioned product can be prepared also in a freeze dried form, and then reconstituted and administered as indicated for the aqueous form, or incorporated in delivery systems (e.g. liposomes), or as a powder that is incorporated in an inert excipient, e.g., lactose, to be administered by the nasal or bronchial route by a special device, or formulated in tablets optionally with rapid dissolution for a sublingual/oromucosal administration, or capsules that are optionally made gastro-resistant through a suitable procedure for oral administration, or as biofilms or mucoadhesive powders to increase the contact time with the buccal mucosa and facilitate the interaction with the local dendritic cells.

The above-mentioned product can be also prepared in the form of oily suspension, syrup, elixir, with optional addition of excipients or substances to make it palatable for a sublingual, oromucosal, or oral administration.

The above-mentioned product can also be associated or conjugated to substances that are known to express an adjuvant activity of the Th1 or Treg type, such as, for es. CpG, bacteria derivatives, micobacteria, micoplasma, *Neisseria*, virus or protozoa, included non-methylated CpG, lipoproteins, or triacylated lipopeptides, lipopolysaccharides (LPS) and derivatives of the lipid A type, synthesis substances, such as imiquimod, resiquimod, poly (I:C).

The composition of the invention will generally be able to contain various excipients and/or carriers adapted to the type of administration selected, according to what is known to those skilled in the art, and what is reported, for example, in Remington's Pharmaceutical Sciences Handbook, Mack Pub. Co., N.Y., USA, 17th edition, 1985.

In all these pharmaceutical formulations, the preparation of the invention will be able to be present in amounts ranging between 0.5 µg (minimum dose) and 200 µg (maintenance dose) of total protein, according to the administration route that is used in the implementation of the specific immunotherapy.

The invention claimed is:

1. A method of obtaining a modified allergen having reduced allergenicity compared to corresponding raw native allergenic material, wherein the raw native allergenic material is selected from the group consisting of DP mites extract, Der p1, ovalbumin, and Lipid Transfer Protein (LTP), wherein
    a part of the primary amine groups of the lysine residues of the raw native allergenic material are functionalized with carbamoyl moieties, the average percentage of functionalized primary amine groups of the lysine residues being, in the range of 50% to 80%; and
    a part of the primary amine groups of the arginine residues of the carbamoyl functionalized allergenic material are further functionalized with dialdehyde moieties, the average percentage of the functionalized arginine residues ranging between 35% and 50%,
    wherein the said functionalization of the primary amine groups of the lysine and arginine residues is performed by the steps of:
    a) when the raw native allergenic material is DP mites extract, buffering the DP mites extract at a pH of 6.86 to reach a protein concentration of 2.5 mg/mL and gel filtering the extract to remove the low molecular weight compounds
    b) performing in a sealed container a carbamylation reaction with potassium cyanate and sodium tetraborate of the part of the lysine residues of a raw native allergenic material, at a temperature ranging between 35° C. and 50° C., for a total reaction time ranging between 16 and 24 hours, where the final concentration of the potassium cyanate ranges between 0.4 M and 0.8 M at a pH between 9 and 9.6;
    c) gel-filtering the product of step b);
    d) subsequently reacting the part of the arginine residues of said allergenic material of the step c) with phenylglyoxal dissolved in a PGO-solubizing solvent in a molar excess of about 800 with respect to the proteins of the allergenic material, at a pH of about 8, for a period of time of about 4 hours, at a temperature of about 25° C.;
    e) gel-filtering or dialyzing the product of step d).

* * * * *